United States Patent
Kumar et al.

(10) Patent No.: US 9,416,105 B2
(45) Date of Patent: Aug. 16, 2016

(54) PROCESS FOR PREPARATION OF SAXAGLIPTIN AND ITS HYDROCHLORIDE SALT

(71) Applicant: Amneal Pharmaceuticals LLC, Bridgewater, NJ (US)

(72) Inventors: Agarwal Virendra Kumar, Gujarat (IN); Siddiqui Arif Badrulhusan, Gujarat (IN); Kataria Lalit Keshav, Gujarat (IN); Maheta Abhay Subodhbhai, Gujarat (IN); Butani Pankaj Changanbhai, Gujarat (IN); Patil Shashikant Prabhakarrao, Maharashtra (IN); Patil Tushar Yashwant, Maharashtra (IN); Deore Ganesh Suryakant, Maharashtra (IN); Pansuriya Ketan Jahyantibhai, Gujarat (IN); Patel Hitesh Sureshbhai, Gujarat (IN); Sondharava Lalit Badhabhai, Gujarat (IN)

(73) Assignee: Amneal Pharmaceuticals LLC, Bridgewater, NJ (US)

( * ) Notice: Subject to any disclaimer, the term of this patent is extended or adjusted under 35 U.S.C. 154(b) by 0 days.

(21) Appl. No.: 14/911,918

(22) PCT Filed: Aug. 28, 2014

(86) PCT No.: PCT/US2014/053123
§ 371 (c)(1),
(2) Date: Feb. 12, 2016

(87) PCT Pub. No.: WO2015/031595
PCT Pub. Date: Mar. 5, 2015

(65) Prior Publication Data
US 2016/0194282 A1    Jul. 7, 2016

(30) Foreign Application Priority Data
Aug. 28, 2013 (IN) .......................... 2813/MUM/2013

(51) Int. Cl.
*C07D 209/52* (2006.01)
*C07C 229/36* (2006.01)

(52) U.S. Cl.
CPC ............ *C07D 209/52* (2013.01); *C07C 229/36* (2013.01); *C07C 2103/74* (2013.01)

(58) Field of Classification Search
None
See application file for complete search history.

(56) References Cited

U.S. PATENT DOCUMENTS

| | | | |
|---|---|---|---|
| 6,395,767 B2 | 5/2002 | Robl et al. |
| 7,186,846 B2 | 3/2007 | Sharma et al. |
| 7,214,702 B2 | 5/2007 | Sharma |
| 7,705,033 B2 | 4/2010 | Truc et al. |
| 8,278,462 B2 | 10/2012 | Vu et al. |
| 2005/0090539 A1 | 4/2005 | Vu et al. |
| 2005/0267191 A1 | 12/2005 | Sharma |
| 2013/0023671 A1 | 1/2013 | Kovi et al. |

FOREIGN PATENT DOCUMENTS

| WO | WO 01/68603 | 9/2001 |
|---|---|---|
| WO | WO 2011/140328 | 11/2011 |

OTHER PUBLICATIONS

PCT International Preliminary Report on Patentability in PCT/US2014/053123, dated Mar. 1, 2016, 7 pages.
PCT International Search Report in PCT/US2014/053123, mailed Dec. 12, 2014, 7 pages.
PCT International Written Opinion in PCT/US2014/053123, dated Dec. 12, 2014, 6 pages.
Specification of Indian Appln. No. 2065/CHE/2012, 5 pages.
Fukushima, H, et al., Synthesis and structure-activity relationships of potent 3- or 4-substituted-2-cyanopyrrolidine dipeptidyl peptidase IV inhibitors, *Bioirg Med Chem.* 12(23) 2004, 6053-61.
Savage, Scott A., et al., Preparations of Saxagliptin, a Novel DDP-IV Inhibitor, *Org. Process Res. Dev.* 13(6) 2009, 1169-1176.

*Primary Examiner* — Rebecca Anderson
*Assistant Examiner* — Po-Chih Chen
(74) *Attorney, Agent, or Firm* — Servilla Whitney LLC

(57) ABSTRACT

Described is an improved and industrially feasible process for the preparation of Saxagliptin or its hydrochloride salt. Also described are the novel intermediates and their use in the preparation of Saxagliptin or its hydrochloride salt.

22 Claims, No Drawings

PROCESS FOR PREPARATION OF SAXAGLIPTIN AND ITS HYDROCHLORIDE SALT

CROSS-REFERENCE TO RELATED APPLICATIONS

This application is the National Stage entry of PCT/US14/53123, filed on Aug. 28, 2014, which claims priority to Indian Application Number 2813/MUM/2013, filed on Aug. 28, 2013.

TECHNICAL FIELD

The present invention relates to processes for the preparation of saxagliptin and its hydrochloride salt. The present invention also relates to intermediate compounds and their use in processes for preparing saxagliptin.

BACKGROUND

Dipepeptidyl peptidase IV inhibitors (DPP-IV inhibitors) are a class of oral hypoglycemic agents that block the enzyme DPP-IV and have been used to treat diabetes mellitus type 2. Saxagliptin has the chemical names (1S,3S,5S)-2-[2(S)-2-amino-2-(3-hydroxy-adamantan-1-yl)acetyl]-2-azabicyclo[3.1.0]hexane-3-carbonitrile or (1S,3S,5S)-2-[(2S)-2-amino-2-(3-hydroxytricyclo[3.3.1.1$^{3,7}$]dec-1-yl)acetyl]-2-azabicyclo[3.1.0]hexane-3-carbonitrile and the structural formula [I]. It is an orally active reversible DPP-IV inhibitor that is the active ingredient in the form of its hydrochloride salt in the ONGLYZA® tablet products originally developed by Bristol-Myers Squibb, and now marketed by AstraZeneca.

[I]

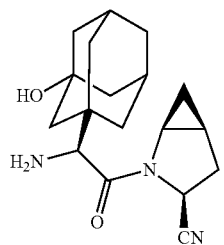

Saxagliptin and its hydrochloride and trifluoroacetic acid salts are disclosed in U.S. Pat. No. 6,395,767. U.S. Pat. No. 7,420,079 and U.S. Pat. No. 8,278,462 disclose a process for the preparation of saxagliptin, its hydrochloride salt, trifluoroacetate, and benzoate salts, and saxagliptin monohydrate. U.S. Pat. No. 7,705,033 discloses a process for the preparation of saxagliptin monohydrate. U.S. Pat. No. 7,214,702 discloses a process for the preparation of saxagliptin or its hydrochloride salt.

The above documents disclose a process for the preparation of saxagliptin, which involves condensation of 2-azabicyclo[3.1.0]hexane-3-carboxylic acid amide with adamantan-1-yl-tert-butoxycarbonylamino acetic acid.

U.S. Pat. No. 7,186,846 discloses a process for the preparation of saxagliptin which involves reacting 2-aza-bicyclo[3.1.0]hexane-3-carbonitrile with trifluoroacetic acid 3-[carboxy-(2,2,2-trifluoroacetylamino)-methyl]adamantan-1-yl ester, followed by reductive cleavage of protected saxagliptin.

Hiroshi Fukushima et al., "Synthesis and Structure—Activity Relationships of Potent 1-(2-Substituted-aminoacetyl)-4-fluoro-2-cyanopyrrolidine Dipeptidyl Peptidase IV Inhibitors," *Chemical and Pharmaceutical Bulletin*, Vol. 56(8), pages 1110-1117 (2008), reports the instability of 2-cyanofluoropyrrolidine derivatives at pH 6-8, due to intramolecular cyclization of basic nitrogen to a cyano group, leading to the formation of cyclic amidine which further transforms to diketopiperazine derivatives. Saxagliptin, being a 2-cyanopyrrolidine derivative, may undergo intramolecular cyclization to form a cyclic amidine.

The above reported processes suffer from the drawback that the tert-butyloxy carbonyl ("BOC") group is too sensitive in acidic conditions, which exist during the condensation of 2-aza-bicyclo[3.1.0]hexane-3-carboxylic acid amide with adamantan-1-yl-tert-butoxycarbonylamino acetic acid, which leads to formation of unwanted impurities. Further, deprotection of BOC requires harsh and more acidic conditions. Moreover, using BOC as a protecting group makes the reaction monitoring difficult using thin layer chromatography ("TLC") and tedious since it is less sensitive to ultraviolet ("UV"). BOC also is relatively expensive, making the process not viable industrially.

Indian Application 2065/CHE/2012 discloses a process for the preparation of saxagliptin which involves the use of the benzyloxy carbonyl group ("CBZ") for protection of the amino group. However, CBZ deprotection would eventually lead to saxagliptin, which by itself is unstable and prone to intramolecular cyclization. Moreover, CBZ is difficult to handle on an industrial scale because of its liquid state and lacrimating properties.

Therefore, there is a need for improved and industrially feasible processes for the preparation of saxagliptin.

SUMMARY OF THE INVENTION

In one aspect, the present invention provides a process for the preparation of saxagliptin or its hydrochloride salt, comprising:
(a) reacting (1S,3S,5S)-2-[(2S)-2-tritylamino-2-(3-hydroxyadamantan-1-yl)acetyl]-2-azabicyclo[3.1.0]hexane-3-carboxamide [IV]

[IV]

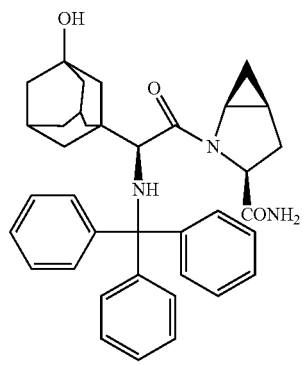

with trifluoroacetic anhydride followed by treatment with a carbonate or bicarbonate salt to obtain (1 S,3S, 5S)-2-[(2S)-2-tritylamino-2-(3-hydroxyadamantan-1-yl)acetyl]-2-azabicyclo[3.1.0]hexane-3-carbonitrile [V]; and

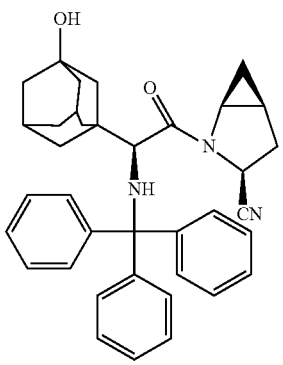

[V]

(b) removing the trityl group from (1S,3S,5S)-2-[(2S)-2-tritylamino-2-(3-hydroxyadamantan-1-yl)acetyl]-2-azabicyclo[3.1.0]hexane-3-carbonitrile [V] to obtain saxagliptin hydrochloride, and optionally converting the hydrochloride salt to saxagliptin.

In one embodiment, (1S,3S,5S)-2-[(2S)-2-tritylamino-2-(3-hydroxyadamantan-1-yl)acetyl]-2-azabicyclo[3.1.0]hexane-3-carboxamide [IV] is prepared by:

reacting 3-hydroxyadamantan-1-yl-tritylamino acetic acid [IIA]

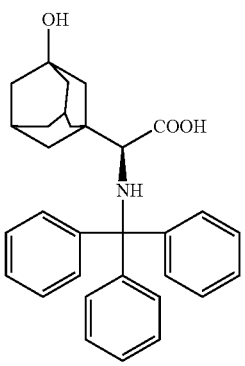

[IIA]

with a methanesulfonic acid salt of (1S,3S,5S)-2-azabicyclo[3.1.0]hexane-3-carboxamide [III],

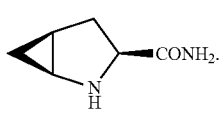

[III]

In another embodiment, 1S,3S,5S)-2-[(2S)-2-tritylamino-2-(3-hydroxyadamantan-1-yl)acetyl]-2-azabicyclo[3.1.0]hexane-3-carboxamide [IV] is prepared by a process, comprising:

reacting 3-hydroxyadamantan-1-yl-tert-butoxycarbonylamino acetic acid [II]

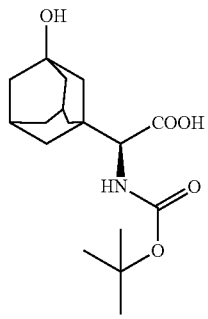

[II]

with a methanesulfonic acid salt of (1S,3S,5S)-2-azabicyclo[3.1.0]hexane-3-carboxamide [III],

[III]

followed by BOC deprotection and reaction with trityl chloride.

In a preferred embodiment, saxagliptin hydrochloride is in the form of saxagliptin hydrochloride dihydrate.

In another aspect, the present invention provides a process for the preparation of saxagliptin or its hydrochloride salt, comprising:
providing (1S,3S,5S)-2-[(2S)-2-tritylamino-2-(3-hydroxyadamantan-1-yl)acetyl]-2-azabicyclo[3.1.0]hexane-3-carbonitrile [V]; and

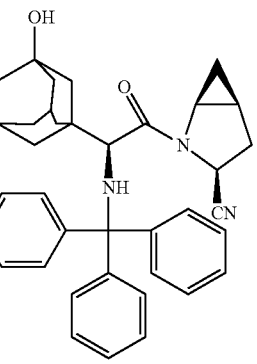

[V]

removing the trityl group from (1S,3S,5S)-2-[(2S)-2-tritylamino-2-(3-hydroxyadamantan-1-yl)acetyl]-2-azabicyclo[3.1.0]hexane-3-carbonitrile [V] to obtain saxagliptin hydrochloride, and optionally converting the hydrochloride salt to saxagliptin.

In additional aspects, the present invention provides intermediate compounds: 3-hydroxyadamantan-1-yl-tritylamino acetic acid [IIA]; (1S,3S,5S)-2-[(2S)-2-tritylamino-2-(3-hydroxyadamantan-1-yl)acetyl]-2-azabicyclo[3.1.0]hexane-3-carboxamide [IV]; and (1S,3S,5S)-2-[(2S)-2-tritylamino-2-(3-hydroxyadamantan-1-yl)acetyl]-2-azabicyclo[3.1.0]hexane-3-carbonitrile [V], and their pharmaceutically acceptable salts, solvates and hydrates thereof; processes for their preparation; and their uses for the preparation of saxagliptin or hydrochloride salt thereof.

DETAILED DESCRIPTION

It is desirable to reduce the formation of the saxagliptin cyclic amidine impurity. It has been found that a triphenylmethyl (trityl) group is superior to other protecting groups in reducing the formation of the cyclic amidine impurity. Moreover, the trityl group is less expensive, easily available, and easy to handle by being in a solid state, thus making it industrially feasible. Further, it is easier to monitor the reaction using TLC or high performance liquid chromatography ("HPLC"), since it absorbs UV light. Moreover, removing a trityl protecting group can directly yield saxagliptin hydrochloride salt and does not involve formation of saxagliptin which is highly unstable and prone to intramolecular cyclization.

The methanesulfonic acid salt of (1S,3S,5S)-2-azabicyclo[3.1.0]hexane-3-carboxamide [III] used in the present process can be obtained by reacting tert-butyl (1S,3S,5S)-3-carbamoyl-2-azabicyclo[3.1.0]hexane-2-carboxylate with methanesulfonic acid in the presence of an organic solvent. Organic solvents that may be used include, but are not limited to, methanol, ethanol, isopropanol, n-butanol, iso-butanol, tert-butanol, and the like. Useful temperatures for conducting the reaction are above about 50° C., such as about 60-70° C., or other temperatures.

In one aspect, the present invention provides a process for the preparation of saxagliptin or its hydrochloride salt, comprising:

(a) reacting (1S,3S,5S)-2-[(2S)-2-tritylamino-2-(3-hydroxyadamantan-1-yl)acetyl]-2-azabicyclo[3.1.0]hexane-3-carboxamide [IV]

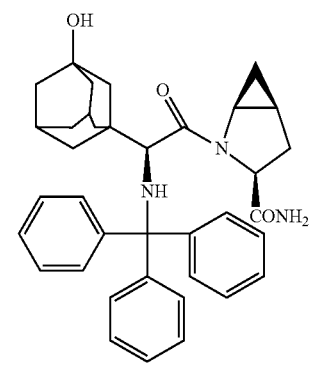

[IV]

with trifluoroacetic anhydride followed by treatment with a carbonate or bicarbonate salt to obtain (1 S,3S,5S)-2-[(2S)-2-tritylamino-2-(3-hydroxyadamantan-1-yl)acetyl]-2-azabicyclo[3.1.0]hexane-3-carbonitrile [V]; and

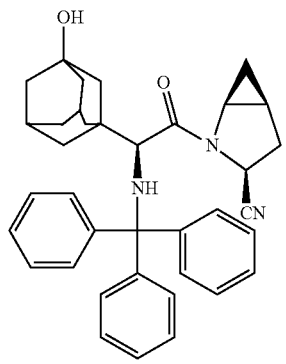

[V]

(b) removing the trityl group from (1S,3S,5S)-2-[(2S)-2-tritylamino-2-(3-hydroxyadamantan-1-yl)acetyl]-2-azabicyclo[3.1.0]hexane-3-carbonitrile [V] to obtain saxagliptin hydrochloride, and optionally converting the hydrochloride salt to saxagliptin.

In one embodiment, (1S,3S,5S)-2-[(2S)-2-tritylamino-2-(3-hydroxyadamantan-1-yl)acetyl]-2-azabicyclo[3.1.0]hexane-3-carboxamide [IV] is prepared by:

reacting 3-hydroxyadamantan-1-yl-tritylamino acetic acid [IIA]

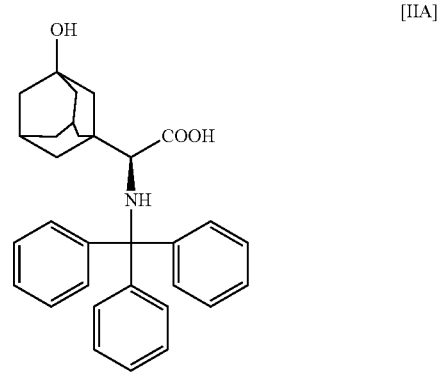 [SMILES: O=C(O)[C@@H](NC(c1ccccc1)(c1ccccc1)c1ccccc1)C12CC3CC(CC(O)(C3)C1)C2]

[IIA]

with a methanesulfonic acid salt of (1S,3S,5S)-2-azabicyclo[3.1.0]hexane-3-carboxamide [III],

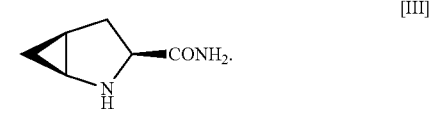

[III]

The compound [IIA] can be prepared by reacting (1S)-α-amino-3-hydroxyadamantane-acetic acid with triphenylmethyl chloride in the presence of a suitable solvent such as dichloromethane and base such as triethylamine at a temperature of about 25-35° C.

The reaction of compound [IIA] and compound [III] can be carried out in the presence of one or more halogenated solvents, such as dichloromethane, 1,2-dichloroethane, 1,1-dichloroethane, chloroform, carbon tetrachloride, and the like, at temperatures about 20-40° C. or about 25-35° C.

The amide formation can be carried out in the presence of a carbodimide coupling agent, such as 1-ethyl-3-(3-dimethylaminopropyl)carbodiimide (EDC), N,N'-dicyclohexylcarbodiimide (DCC), or N,N'-diisopropylcarbodiimide (DIC). Further, an additional auxiliary nucleophile, such as 1-hydroxybenzotriazole, N-hydroxysuccinimide, or 1-hydroxy-7-azabenzotriazole, can be added to the reaction mixture to prevent loss of optical purity.

The amide bond formation can be carried out in the presence of a tertiary amine base such as N-methylmorpholine (NMM), N,N-diisopropylethylamine (DIPEA or Hünig's base), and triethylamine (TEA).

In another embodiment, (1S,3S,5S)-2-[(2S)-2-tritylamino-2-(3-hydroxyadamantan-1-yl)acetyl]-2-azabicyclo[3.1.0]hexane-3-carboxamide [IV] is prepared by:
reacting 3-hydroxyadamantan-1-yl-tert-butoxycarbonylamino acetic acid [II]

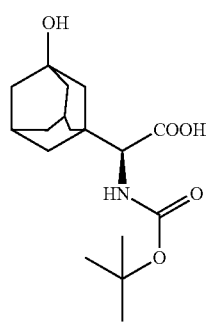

[II]

with a methanesulfonic acid salt of (1S,3S,5S)-2-azabicyclo[3.1.0]hexane-3-carboxamide [III],

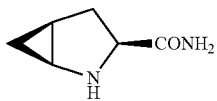

[III]

followed by BOC deprotection and reaction with trityl chloride.

The reaction of compound [II] and compound [III] can be carried out in the presence of one or more halogenated solvents, such as dichloromethane, 1,2-dichloroethane, 1,1-dichloroethane, chloroform, carbon tetrachloride, and the like, at temperatures about 20-40° C. or about 25-35° C.

The amide formation can be carried out in the presence of a carbodimide coupling agent, such as 1-ethyl-3-(3-dimethylaminopropyl)carbodiimide (EDC), N,N'-dicyclohexylcarbodiimide (DCC), or N,N'-diisopropylcarbodiimide (DIC). Further, an additional auxiliary nucleophile, such as 1-hydroxybenzotriazole, N-hydroxysuccinimide, or 1-hydroxy-7-azabenzotriazole, can be added to the reaction mixture to prevent loss of optical purity.

The amide bond formation can be carried out in the presence of a tertiary amine base such as N-methylmorpholine (NMM), N,N-diisopropylethylamine (DIPEA or Hünig's base), and triethylamine (TEA).

The removal of BOC protecting group after completion of the reaction of the compound [II] and [III] can be carried out with a solution of hydrochloric acid, such as an aqueous solution having a concentration of HCl about 34-36% by weight followed by treatment with hydrogen chloride in isopropanol in concentration of about 14.2% w/w. The formation of compound [IV] can be carried out by treatment of reaction mass with trityl chloride in presence of suitable base such as triethylamine and suitable solvent such as acetonitrile at a temperature of about 10-20° C.

The conversion of compound [IV] to compound [V] involves treatment with trifluoroacetic anhydride in the presence of an organic solvent and a base. Useful organic solvents include, but are not limited to, methanol, ethanol, n-propanol, isopropyl alcohol, isobutanol, n-butanol, tert-butanol, amyl alcohol, isoamyl alcohol, hexanol, tetrahydrofuran, acetone, methyl ethyl ketone, methyl isobutyl ketone, methyl tert-butyl ketone, ethyl acetate, methyl acetate, isopropyl acetate, tert-butyl acetate, ethyl formate, and mixtures of two or more thereof. The base is an organic or inorganic base. Exemplary organic bases include, without limitation, triethyl amine, tributyl amine, ammonia, diisopropyl amine, dimethyl amine, diisopropyl ethyl amine, pyridine, and the like.

Trifluoroacetic acid generated during the conversion of compound [IV] to compound [V] can be scavenged using an aqueous solution of alkali metal carbonates or bicarbonates such as sodium carbonate, sodium bicarbonate, potassium carbonate, potassium bicarbonate, and the like. In one embodiment, trifluoroacetic acid generated during the reaction can be scavenged using a 20% aqueous potassium carbonate solution. Completion of scavenging can be confirmed by TLC.

The compound (1S,3S,5S)-2-[(2S)-2-tritylamino-2-(3-hydroxyadamantan-1-yl)acetyl]-2-azabicyclo[3.1.0]hexane-3-carbonitrile [V] can optionally be further purified using an alcohol, such as methanol.

The removal of the trityl protecting group from compound [V] can be carried out with a solution of hydrochloric acid, such as an aqueous solution having a concentration of HCl about 34-36% by weight. Examples of solvents that can be used in the deprotection step include methanol, ethanol, isopropanol, n-butanol, and iso-butanol. The deprotection step can be carried out at temperatures about 20-35° C., or about 25-30° C. Saxagliptin hydrochloride, obtained as a residue after distilling the solvent in the deprotection step, can be further purified using an ester, such as methyl acetate, ethyl acetate, and isopropyl acetate as antisolvents. In a preferred embodiment, saxagliptin hydrochloride is recovered as saxagliptin hydrochloride dihydrate. The recovered saxagliptin hydrochloride can optionally be converted to saxagliptin using methods known in the art. In yet another aspect, the present invention provides a process for preparation of saxagliptin hydrochloride as depicted in the scheme-I below.

Scheme-I
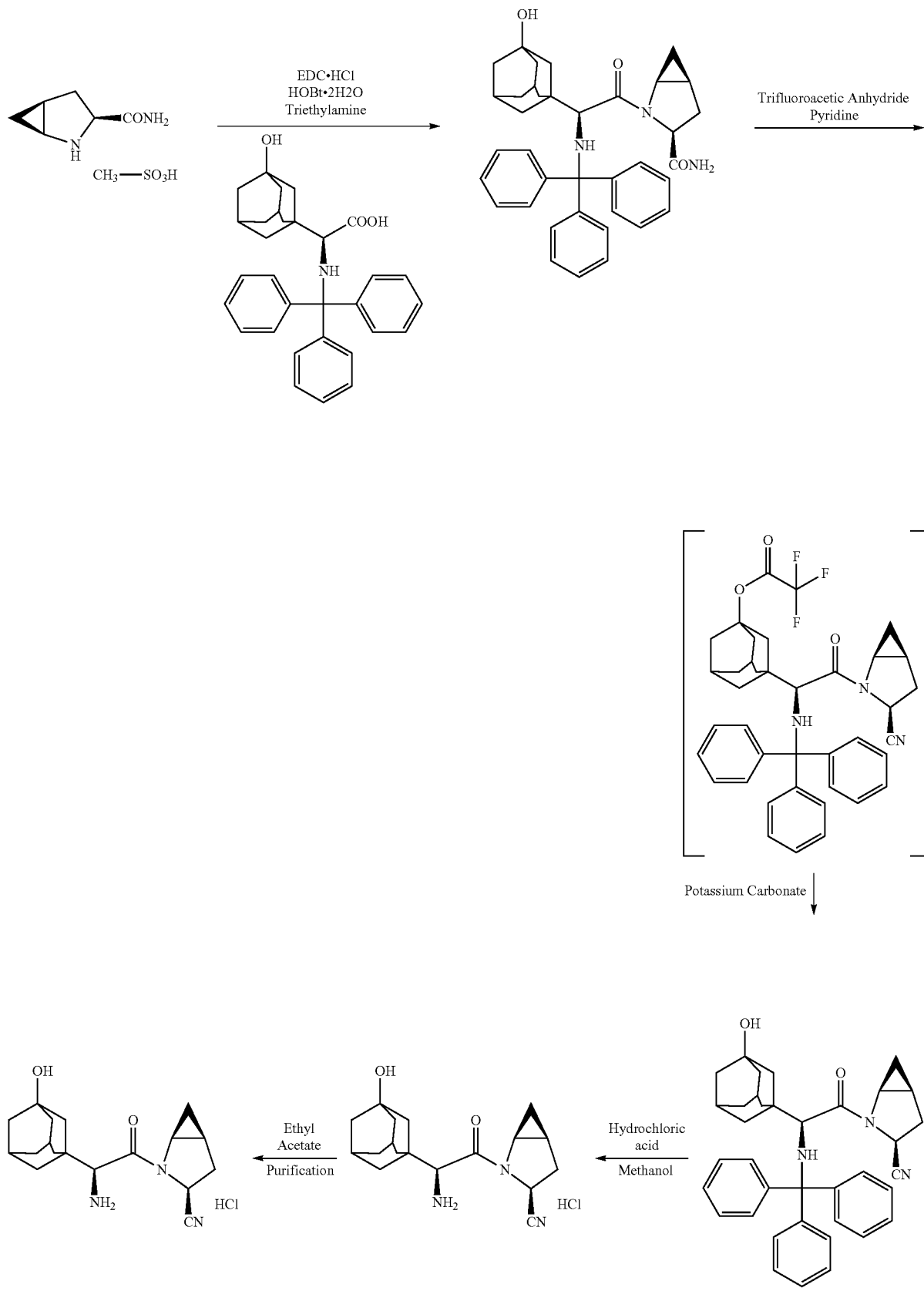

In yet another aspect, the present invention provides a process for preparation of saxagliptin hydrochloride as depicted int he scheme-II below.

dichloromethane (10 ml) at 10-20° C. was mixed with 20-25% isopropanol-HCl (2 ml) and stirred at 25-35° C. for 8 hours. Solvent was evaporated from the reaction mixture to Scheme-II

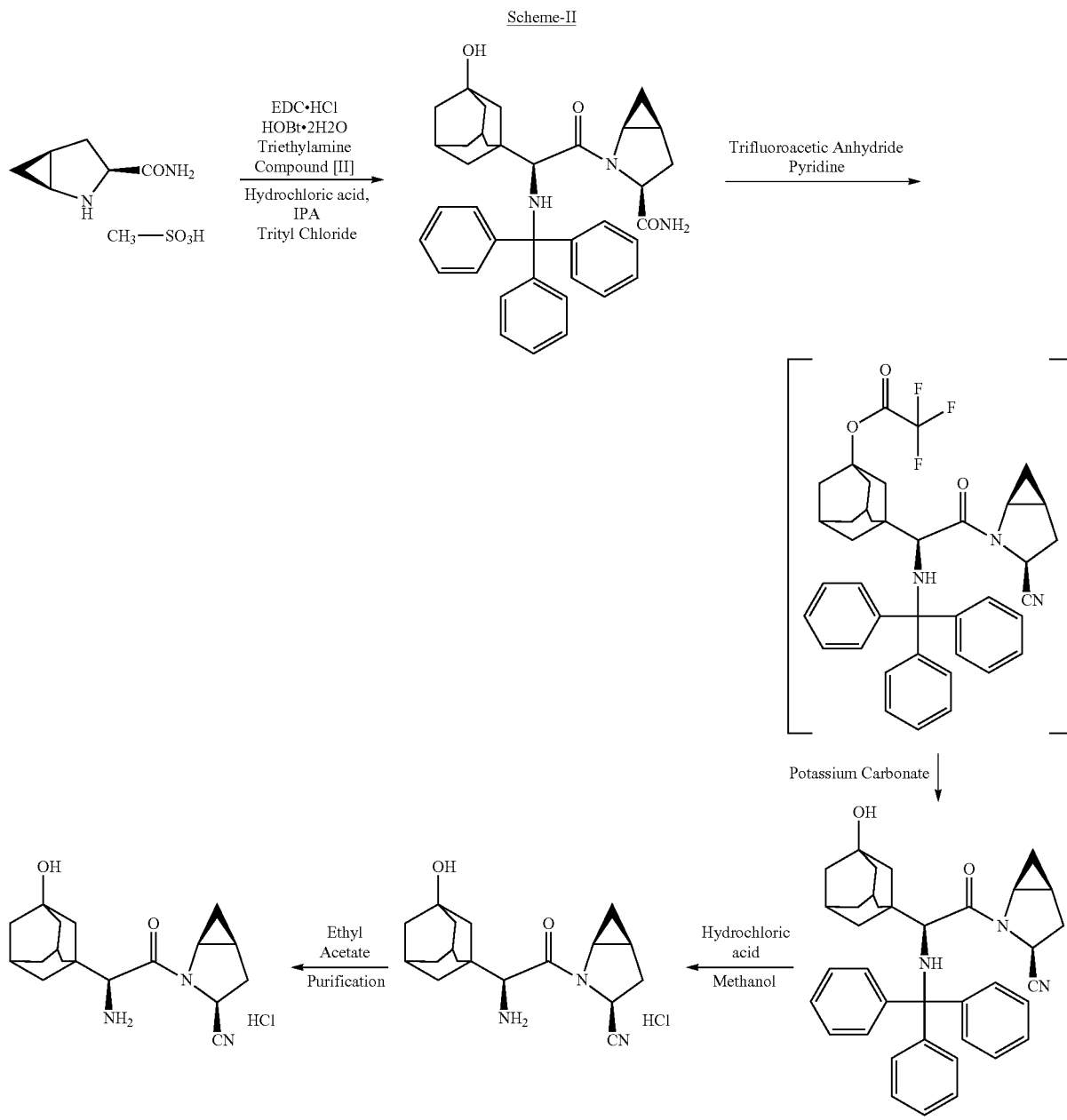

The following examples are provided only for the purpose of illustrating certain specific aspects and embodiments of the present invention and should not be considered as limiting the scope or spirit of the invention in any manner.

give the product (1S)-α-amino-3-hydroxyadamantane-acetic acid hydrochloride as a solid (0.72 g). (Yield: 90.0%)

Example 1

Preparation of (1S)-α-amino-3-hydroxyadamantane-acetic acid hydrochloride

A solution of (1S)-1-[[(1,1-Dimethylethoxy)carbonyl]amino]-3-hydroxyadamantane-1-acetic acid (1.0 g) in Example 2

Preparation of (1S)-1-[triphenylmethyl amino]-3-hydroxyadamantane-1-acetic acid

A solution of (1S)-α-amino-3-hydroxyadamantane-acetic acid (1.0 g) in dichloromethane (10 ml) at 15-25° C. was mixed with triethylamine (1.18 ml) and triphenylmethyl chloride (1.2 g). The reaction mixture was stirred at 25-35° C. for 4 hours. Solvent was evaporated from the reaction mixture to give the product (1S)-1-[triphenylmethyl amino]-3-hydroxy-adamantane-1-acetic acid (1.24 g). (Yield: 70.0%)

Example 3

Preparation of methanesulfonic acid salt of (1S,3S,5S)-2-azabicyclo[3.1.0]hexane-3-carboxamide Tert-butyl (1S,3S,5S)-3-carbamoyl-2-azabicyclo[3.1.0]hexane-2-carboxylate (100 g, 0.442 mole) was combined with isopropyl alcohol (600 ml), with stirring at 25-30° C. The mixture was heated to 60-70° C. and methanesulfonic acid (55.2 g, 0.575 mole) was added in small amounts over 60 minutes. The mixture was stirred for 4 hours at 60-70° C. Completion of the reaction was confirmed using TLC. The mixture was cooled to 5-15° C. and stirred for 1 hour. The mixture was filtered and the solid was washed with chilled isopropyl alcohol (2×50 ml). The filtrate was dried under vacuum to obtain the methanesulfonic acid salt of (1S,3S,5S)-2-azabicyclo[3.1.0]hexane-3-carboxamide. (Yield=96.7%; HPLC purity=96%)

Mass: 434 [M+H]$^+$ $^1$H-NMR (CDCl$_3$) δ: 6.96 (1H, s), 5.68 (1H, s), 5.39-5.42 (1H, d), 4.88-4.91 (1H, dd), 4.52-4.54 (1H, d), 3.67-3.70 (1H, m), 2.50-2.53 (1H, dd), 2.22 (2H, s), 2.03 (1H, s), 1.47-1.75 (15H, m), 1.41 (9H, s), 1.24 (1H, s), 0.81-0.95 (2H, m)

Example 4

Preparation of (1S,3S,5S)-2-[(2S)-2-triphenylmethyl-amino-2-(3-hydroxyadamantan-1-yl)acetyl]-2-azabicyclo[3.1.0]hexane-3-carboxamide A solution of (1S)-1-[triphenylmethyl amino]-3-hydroxy-adamantane-1-acetic acid (1.0 g), (1S,3S,5S)-2-azabicyclo[3.1.0]-hexane-3-carboxamide methanesulphonate (0.47 g), 1-hydroxybenzotriazole monohydrate (HOBt.H2O) (0.08 g), dichloromethane (5 ml), and triethyl amine (0.4 ml) at 5-15° C. was combined with triethylamine (0.65 ml) and 1-ethyl-3-(3-dimethylaminopropyl) carbodiimide hydrochloride (EDC.HCl) (0.5 g) and stirred at ambient temperature (25-35° C.) for 12 hours. Completion of the reaction was verified using TLC. The reaction mixture was successively washed with water (5 ml), 1N HCl (5 ml), 5% aqueous sodium bicarbonate solution (3×5 ml), and then with brine (5 ml). The solvent from the organic phase was evaporated to give a residue. To the residue was added toluene (5 ml) and water (5 ml) and the mixture was heated to 45-55° C. and maintained for 1 hour. The mixture was cooled to 25° C., stirred for 2 hours and filtered. The solid was washed with toluene (2 ml) and dried at 50-60° C. in an oven to give the title compound (0.984 g). (Yield: 80.0%)

Example 5

Preparation of (1S,3S,5S)-2-[(2S)-2-(tritylamino)-2-(3-hydroxyadamantan-1-yl)acetyl]-2-azabicyclo[3.1.0]hexane-3-carboxamide 1-Ethyl-3-(3-dimethylaminopropyl) carbodiimide hydrochloride (EDC.HCl) (1.2 eq., 12.3 g) was added in portions to a solution of 3-hydroxyadamantane-1-yl (1S)-tritylamino-acetic acid (25.0 g) in tetrahydrofuran (175 ml) and stirred for 15 minutes. 1-Hydroxybenzotriazole monohydrate (HOBt.H2O) (1.0 eq., 8.2 g) and (1S,3S,5S)-2-azabicyclo[3.1.0]-hexane-3-carboxamide methanesulphonate (1.0 eq., 11.88 g) were added to the mixture in portions. Triethyl amine (3.2 eq., 17.28 g) was added dropwise to the reaction mixture over 20 minutes. The reaction mixture was stirred at 25° C. for 5 hours. Completion of the reaction was verified using TLC. The solvent was distilled from the reaction mixture to give a residue. Dichloromethane (250 ml) and water (100 ml) were mixed with the residue and the organic phase was separated. The organic phase was washed with aqueous dilute HCl (100 ml), aqueous 10% sodium bicarbonate solution (100 ml), and then with brine (100 ml). The organic phase was dried over sodium sulfate and the solvent evaporated to give a residue, which was dried under high vacuum at 30-40° C. for 2 hours to obtain (1S,3S,5S)-2-[(2S)-2-(tritylamino)-2-(3-hydroxy-adamantan-1-yl)acetyl]-2-azabicyclo[3.1.0]hexane-3-carboxamide (18.0 g).

(Yield: 59%)

Example 6

Preparation of (1S,3S,5S)-2-[(2S)-2-tritylamino-2-(3-hydroxyadamantan-1-yl)acetyl]-2-azabicyclo[3.1.0]hexane-3-carboxamide Tert-butoxycarbonylamino-(3-hydroxy-adamantan-1-yl)-acetic acid (100 g; 0.307 mole) was added to dichloromethane (500 ml) with stirring. The methanesulfonic acid salt of (1S,3S,5S)-2-azabicyclo[3.1.0]hexane-3-carboxamide (64.8 g; 0.292 mole) was added, and the reaction mixture was stirred for 15 minutes at 25-35° C. In a separate flask, 1-hydroxy-benzotriazole monohydrate (11.8 g; 0.077 mole) and triethylamine (34.2 g) were added to dichloromethane (500 ml) and stirred to form a solution. This solution was added to the reaction mixture gradually over 30 minutes at 25-30° C. The reaction mixture was then cooled to 5-15° C., 1-ethyl-3-(3-dimethylaminopropyl)carbodiimide hydrochloride (EDC.HCl) (70.6 g) was added, and the mixture was stirred for 15 minutes at 5-15° C. Triethylamine (65.2 g) was added to the reaction mixture and stirred for 30 minutes. Temperature of the reaction mixture was raised to 25-35° C. and stirred continuously for 12 hours. Reaction completion was confirmed by HPLC. Water (500 ml) was added, the mixture was stirred, and the organic layer was separated. The organic layer was washed with dilute hydrochloric acid solution (500 ml, prepared by adding concentrated hydrochloric acid (60 ml) to water (440 ml)), and further washed with sodium bicarbonate solution (3 times), followed by washing with sodium chloride solution. Hydrogen chloride in isopropanol (14.2% w/w, 315.6 g) was added over 60 minutes, and the mixture was stirred for 4 hours. Completion of the reaction was confirmed by HPLC. The mixture was distilled under vacuum to remove dichloromethane. Toluene was added to the residue and distilled under vacuum. Acetonitrile (400 ml) was added to the residue followed by addition of triethylamine (79.2 g) over 15 minutes with stirring. The reaction mixture was cooled to 10-20° C., and trityl chloride (72.7 g) was added gradually, followed by stirring for 2 hours. Completion of the reaction was confirmed by HPLC. The mixture was distilled under vacuum to remove acetonitrile. Toluene was added to the residue and distilled under vacuum. Toluene (500 ml) followed by water (500 ml) were added to the residue, the mixture was heated at 45-55° C. and filtered and dried to obtain the product. (Yield=60.3%; HPLC purity=94%)

Mass: 576 [M+H]$^+$ $^1$H-NMR (CD$_3$OD) δ: 7.43-7.45 (5H, d), 7.06-7.17 (10H, m), 4.50 (1H, s), 3.84-3.87 (1H, dd), 3.42 (1H, s), 3.09-3.13 (1H, m), 2.87-2.91 (1H, m), 2.15-2.23 (1H, m), 2.09 (1H, s), 1.90-1.92 (1H, d), 1.42-1.77 (13H, m), 1.19-1.22 (1H, t), 0.72-0.76 (1H, m), 0.50-0.55 (1H, m)

Example 7

Preparation of (1S,3S,5S)-2-[(2S)-2-tritylamino-2-(3-hydroxyadamantan-1-yl)acetyl]-2-azabicyclo[3.1.0]hexane-3-carbonitrile A solution of (1S,3S,5S)-2-[(2S)-2-tritylamino-2-(3-hydroxyadamantan-1-yl)acetyl]-2-azabicyclo[3.1.0]hexane-3-carboxamide (15.0 g) in tetrahydrofuran (150 ml) was mixed with pyridine (12.3 g) and cooled to 0-10° C. Trifluoroacetic anhydride (19.1 g) was added to the reaction mixture slowly over 30 minutes. The reaction mixture was stirred at 0-10° C. for 3 hours. Completion of the reaction was confirmed by HPLC. Aqueous potassium carbonate solution (20%, 240 ml) was added to the reaction mixture over 30 minutes to obtain pH 10-11. Methanol (50 ml) was added, and the reaction mixture was stirred at 25° C. for 3 hours. Completion of the reaction was verified using TLC. The reaction mixture was cooled to 0° C. and stirred for 30 minutes. The solid was filtered and washed with water (2×15 ml). The solid was dried under vacuum at 50-60° C. for 8 hours to give the title compound (10.0 g).

(Yield=79%; HPLC purity=99%)

Mass: 558 [M+H]$^+$ $^1$H-NMR (DMSO d$_6$) δ: 7.47-7.49 (6H, d), 7.24-7.28 (6H, t), 7.16-7.19 (3H, t), 4.46 (1H, s), 4.05-4.08 (1H, dd), 3.10-3.13 (1H, m), 2.95-2.98 (1H, d), 2.20-2.26 (1H, m), 2.12-2.18 (2H, m), 1.88-1.95 (3H, m), 1.38-1.75 (1H, m), 0.75-0.80 (1H, q), 0.42-0.46 (1H, m)

Example 8

Preparation of Saxagliptin Hydrochloride

A mixture of aqueous hydrochloric acid (34.5% w/w) (2.3 g) and methanol (20 ml) was added to a mixture of (1S,3S,5S)-2-[(2S)-2-tritylamino-2-(3-hydroxyadamantan-1-yl)acetyl]-2-azabicyclo[3.1.0]hexane-3-carbonitrile (10.0 g) in methanol (80 ml), and the mass was stirred at 25° C. for 3 hours. Completion of the reaction was verified by HPLC. Solvent was distilled from the reaction mixture to give a residue. Ethyl acetate (100 ml) was mixed with the residue for 30 minutes at ambient temperature. The solid was filtered and washed with ethyl acetate (2×5 ml). The solid was dried under vacuum at 50-60° C. for 8 hours to give the title product (6.0 g). (Yield=90%; HPLC purity=99.5%)

Mass: 316 [M+H]$^+$ $^1$H-NMR (DMSO d$_6$) δ: 8.29 (3H, s), 5.21-5.24 (1H, dd), 4.63 (1H, s), 4.23 (1H, s), 4.09-4.12 (1H, m), 2.54-2.57 (1H, m), 2.23-2.27 (1H, dd), 2.15 (1H, s), 1.93-1.98 (1H, m), 1.40-1.67 (12H, m), 1.00-1.05 (1H, m), 0.73-0.77 (1H, m)

What is claimed is:

1. A process for the preparation of saxagliptin of formula [I] or its hydrochloride salt,

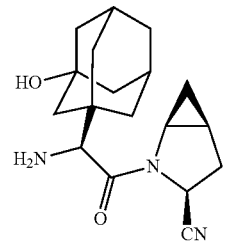

comprising:
a. reacting (1S,3S,5S)-2-[(2S)-2-tritylamino-2-(3-hydroxyadamantan-1-yl)acetyl]-2-azabicyclo[3.1.0]hexane-3-carboxamide [IV]

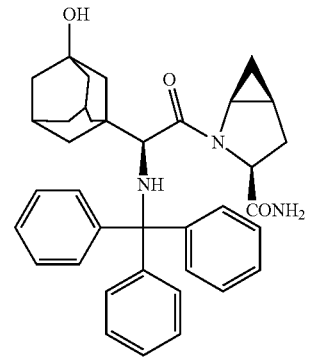

with trifluoroacetic anhydride followed by treatment with a carbonate or bicarbonate salt to obtain (1S,3S,5S)-2-[(2S)-2-tritylamino-2-(3-hydroxyadamantan-1-yl)acetyl]-2-azabicyclo[3.1.0]hexane-3-carbonitrile [V]; and

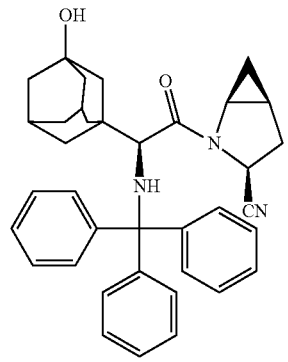

b. removing the trityl group from (1S,3S,5S)-2-[(2S)-2-tritylamino-2-(3-hydroxyadamantan-1-yl)acetyl]-2-azabicyclo[3.1.0]hexane-3-carbonitrile [V] to obtain saxagliptin hydrochloride, and optionally converting the hydrochloride salt to saxagliptin.

2. The process of claim 1, wherein carbonate salt in step (a) is potassium carbonate.

3. The process of claim 1, wherein step (a) is carried out in the presence of an organic or inorganic base.

4. The process of claim 3, wherein the organic or inorganic base is selected from the group consisting of triethyl amine, tributyl amine, ammonia, diisopropyl amine, dimethyl amine, diisopropyl ethyl amine, pyridine, and mixtures thereof.

5. The process of claim 1, wherein removal of the trityl group from (1S,3S,5S)-2-[(2S)-2-tritylamino-2-(3-hydroxyadamantan-1-yl)acetyl]-2-azabicyclo[3.1.0]hexane-3-carbonitrile [V] is carried out in a solution of hydrochloric acid and organic solvent at a temperature of about 20-35° C.

6. The process of claim 1, wherein saxagliptin hydrochloride obtained is in the form of saxagliptin hydrochloride dihydrate.

7. The process of claim 1, further comprising:
reacting 3-hydroxyadamantan-1-yl-tert-butoxycarbonylamino acetic acid [II]

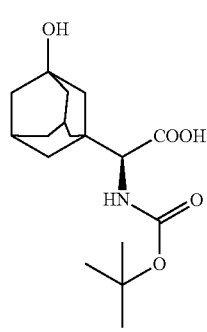

[II]

with a methanesulfonic acid salt of (1S,3S,5S)-2-azabicyclo[3.1.0]hexane-3-carboxamide [III],

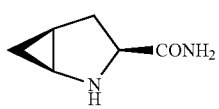

[III]

followed by BOC deprotection and reaction with trityl chloride to obtain (1S,3S,5S)-2-[(2S)-2-tritylamino-2-(3-hydroxyadamantan-1-yl)acetyl]-2-azabicyclo[3.1.0]hexane-3-carboxamide [IV].

8. The process of claim 7, wherein the reaction of 3-hydroxyadamantan-1-yl-tert-butoxycarbonylamino acetic acid [II] and the methanesulfonic acid salt of (1S,3S,5S)-2-azabicyclo[3.1.0]hexane-3-carboxamide [III] is carried out in the presence of a coupling agent selected from the group consisting of 1-ethyl-3-(3-dimethylaminopropyl)carbodiimide (EDC), N,N'-dicyclohexylcarbodiimide (DCC), and N,N'-diisopropylcarbodiimide (DIC).

9. The process of claim 7, wherein the reaction of 3-hydroxyadamantan-1-yl-tert-butoxycarbonylamino acetic acid [II] and the methanesulfonic acid salt of (1S,3S,5S)-2-azabicyclo[3.1.0]hexane-3-carboxamide [III] is carried out in the presence of an auxiliary nucleophile selected from the group consisting of 1-hydroxybenzotriazole, N-hydroxysuccinimide, and 1-hydroxy-7-azabenzotriazole.

10. The process of claim 7, wherein the reaction of 3-hydroxyadamantan-1-yl-tert-butoxycarbonylamino acetic acid [II] and the methanesulfonic acid salt of (1S,3S,5S)-2-azabicyclo[3.1.0]hexane-3-carboxamide [III] is carried out in the presence of an organic or inorganic base.

11. The process of claim 10, wherein the organic or inorganic base is selected from the group consisting of triethyl amine, tributyl amine, ammonia, diisopropyl amine, dimethyl amine, diisopropyl ethyl amine, pyridine, and mixtures thereof.

12. The process of claim 7, wherein the reaction of 3-hydroxyadamantan-1-yl-tert-butoxycarbonylamino acetic acid [II] and the methanesulfonic acid salt of (1S,3S,5S)-2-azabicyclo[3.1.0]hexane-3-carboxamide [III] is carried out in the presence of one or more halogenated solvents and at a temperature of about 20-40° C.

13. The process of claim 7, wherein BOC deprotection is carried out in a solution of hydrochloric acid.

14. The process of claim 7, wherein reaction with trityl chloride is carried out in the presence of an organic solvent and base.

15. The process of claim 1, further comprising:
reacting 3-hydroxyadamantan-1-yl-tritylamino acetic acid [IIA]

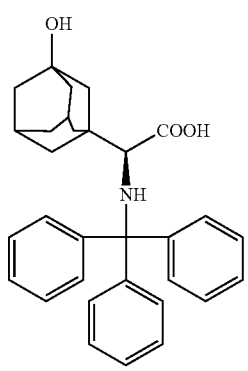

[IIA]

with a methanesulfonic acid salt of (1S,3S,5S)-2-azabicyclo[3.1.0]hexane-3-carboxamide [III],

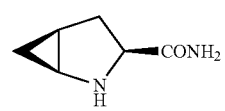

[III]

to obtain (1S,3S,5S)-2-[(2S)-2-tritylamino-2-(3-hydroxyadamantan-1-yl)acetyl]-2-azabicyclo[3.1.0]hexane-3-carboxamide [IV].

16. The process of claim 15, wherein the reaction of 3-hydroxyadamantan-1-yl-tritylamino acetic acid [IIA] and the methanesulfonic acid salt of (1S,3S,5S)-2-azabicyclo[3.1.0]hexane-3-carboxamide [III] is carried out in the presence of a coupling agent selected from the group consisting of 1-ethyl-3-(3-dimethylaminopropyl)carbodiimide (EDC), N,N'-dicyclohexylcarbodiimide (DCC), and N,N'-diisopropylcarbodiimide (DIC).

17. The process of claim 15, wherein the reaction of 3-hydroxyadamantan-1-yl-tritylamino acetic acid [IIA] and the methanesulfonic acid salt of (1S,3S,5S)-2-azabicyclo[3.1.0]hexane-3-carboxamide [III] is carried out in the presence of an auxiliary nucleophile selected from the group consisting of 1-hydroxybenzotriazole, N-hydroxysuccinimide, and 1-hydroxy-7-azabenzotriazole.

18. The process of claim 15, wherein the reaction of 3-hydroxyadamantan-1-yl-tritylamino acetic acid [IIA] and the methanesulfonic acid salt of (1S,3S,5S)-2-azabicyclo[3.1.0]hexane-3-carboxamide [III] is carried out in the presence of an organic or inorganic base.

19. The process of claim 18, wherein the organic or inorganic base is selected from the group consisting of triethyl amine, tributyl amine, ammonia, diisopropyl amine, dimethyl amine, diisopropyl ethyl amine, pyridine, and mixtures thereof.

20. The process of claim 1, wherein the reaction of 3-hydroxyadamantan-1-yl-tritylamino acetic acid [IIA] and the methanesulfonic acid salt of (1S,3S,5S)-2-azabicyclo[3.1.0] hexane-3-carboxamide [III] is carried out in the presence of one or more halogenated solvents and at a temperature of about 20-40° C.

21. A process for the preparation of saxagliptin of formula [I] or its hydrochloride salt,

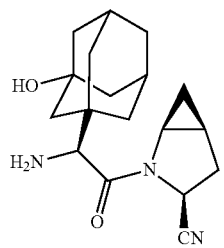

[I]

comprising:
providing (1S,3S,5S)-2-[(2S)-2-tritylamino-2-(3-hydroxyadamantan-1-yl)acetyl]-2-azabicyclo[3.1.0]hexane-3-carbonitrile [V]; and

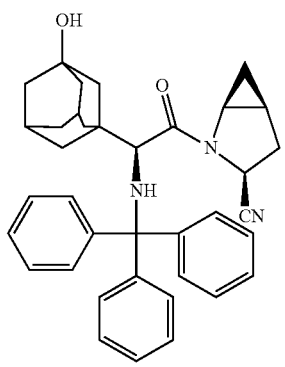

[V]

removing the trityl group from (1S,3S,5S)-2-[(2S)-2-tritylamino-2-(3-hydroxyadamantan-1-yl)acetyl]-2-azabicyclo[3.1.0]hexane-3-carbonitrile [V] to obtain saxagliptin hydrochloride, and optionally converting the hydrochloride salt to saxagliptin.

22. A compound selected from:

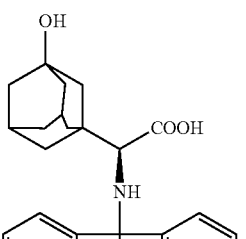

[IIA]

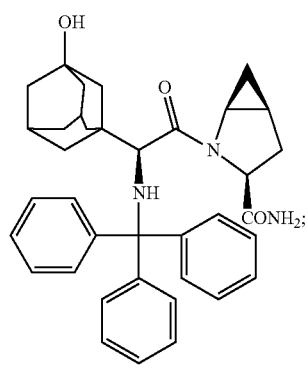

[IV]

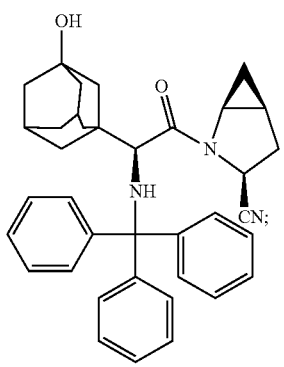

[V]

and pharmaceutically acceptable salts, solvates and hydrates thereof.

* * * * *